(12) United States Patent
Wang et al.

(10) Patent No.: US 10,485,749 B2
(45) Date of Patent: Nov. 26, 2019

(54) COMPOSITION FOR CLEANSING KERATIN MATERIALS WITH IMPROVED RINSING PROPERTIES

(71) Applicant: L'OREAL, Paris (FR)

(72) Inventors: Huifeng Wang, Shanghai (CN); Yuchao Chen, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/774,152

(22) PCT Filed: Dec. 10, 2015

(86) PCT No.: PCT/CN2015/097003
§ 371 (c)(1),
(2) Date: May 7, 2018

(87) PCT Pub. No.: WO2017/096587
PCT Pub. Date: Jun. 15, 2017

(65) Prior Publication Data
US 2018/0333344 A1    Nov. 22, 2018

(51) Int. Cl.
| | | |
|---|---|---|
| *A61K 8/44* | (2006.01) | |
| *A61K 8/81* | (2006.01) | |
| *A61K 8/36* | (2006.01) | |
| *A61Q 19/10* | (2006.01) | |
| *A61K 8/19* | (2006.01) | |
| *A61K 8/42* | (2006.01) | |
| *A61K 8/73* | (2006.01) | |

(52) U.S. Cl.
CPC ............... *A61K 8/817* (2013.01); *A61K 8/19* (2013.01); *A61K 8/36* (2013.01); *A61K 8/361* (2013.01); *A61K 8/42* (2013.01); *A61K 8/44* (2013.01); *A61K 8/442* (2013.01); *A61K 8/732* (2013.01); *A61K 8/8141* (2013.01); *A61K 8/8152* (2013.01); *A61Q 19/10* (2013.01); *A61K 2800/48* (2013.01); *A61K 2800/596* (2013.01)

(58) Field of Classification Search
None
See application file for complete search history.

(56) References Cited

U.S. PATENT DOCUMENTS

| 6,383,995 B1 | 5/2002 | Maurin et al. | |
|---|---|---|---|
| 8,038,989 B2 | 10/2011 | Murray et al. | |
| 2008/0081776 A1 | 4/2008 | Crotty et al. | |
| 2016/0074310 A1* | 3/2016 | Klug ................... | A61K 8/31 510/158 |

FOREIGN PATENT DOCUMENTS

| CN | 1292260 A | 4/2001 | |
|---|---|---|---|
| CN | 102836088 A | 12/2012 | |
| JP | 2008-007649 A | 1/2008 | |
| JP | 2011-084484 A | 4/2011 | |
| JP | 2013-163659 A | 8/2013 | |
| JP | 2014-034560 A | 2/2014 | |
| JP | 2014-125434 A | 7/2014 | |
| WO | WO 2008/145579 A2 | 12/2008 | |
| WO | WO 2014/70025 * | 10/2014 | ............... A61Q 5/02 |
| WO | WO 2014/170025 A1 | 10/2014 | |
| WO | WO-2015071298 A2 * | 5/2015 | ............... A61K 8/31 |
| WO | WO 2015/096115 A1 | 7/2015 | |

OTHER PUBLICATIONS

International Search Report and Written Opinion dated Aug. 23, 2016 in PCT/CN2015/097003 filed Dec. 10, 2015.
Extended European Search Report dated Jun. 13, 2019 in EP 15910062.7, filed Apr. 11, 2018.
Japanese Office Action dated May 7, 2019 in JP 2018-545535, filed May 23, 2018.
Daria Di Vincenzo et al., "Regional Variation in Shea Butter Lipid and Triterpene Composition in Four African Countries", Journal of Agricultural and Food Chemistry, vol. 53, No. 19, 2005, pp. 7473-7479, XP055433042.

* cited by examiner

*Primary Examiner* — Brian Gulledge
(74) *Attorney, Agent, or Firm* — Oblon, McClelland, Maier & Neustadt, L.L.P.

(57) ABSTRACT

A composition for treating a keratin material, comprising at least one amino acid surfactant, at least one amphoteric or zwitterionic surfactant, at least one solid fatty acid, at least one starch phosphates, and at least one acrylic thickening polymer. The composition has an improved rinsing speed after application, and is stable over 2 months, with an improved foaming properties, such as density of foam, and foaming volume.

16 Claims, No Drawings

COMPOSITION FOR CLEANSING KERATIN MATERIALS WITH IMPROVED RINSING PROPERTIES

The present invention relates to a composition for cleansing keratin materials. More particularly, the present invention relates to a composition for cleansing keratin materials, in particular the skin and scalp, with an improved rinsing properties and foaming properties.

PRIOR ART

Cleansing the skin is very important especially for caring for the face. It must be as efficient as possible because greasy residues, such as dirt, excess sebum, and the remnants of cosmetic products used daily, and make-up products can result in an unpleasant oily appearance. The issue of oily appearance of the skin is even more severe on oily skins.

Moreover, nowadays it has become more and more important that cleansing compositions provide effective cleansing of the keratin material as well as mildness for said keratin material.

Efforts have been made to meet the requirements as mentioned above. As a result, mild surfactants, such as amino acid surfactants, are being used more frequently to provide a mild, high satisfactory cleanser. For example, it is known to formulate amino acid surfactant(s) in combination with high level of hydrocarbon wax and oil emollients to obtain a mild foaming cleansing product with good skin sensory after application.

However it is still not satisfying.

The prior art mentioned above is especially not satisfying when applying on oily skin, in particular in terms of rinsing speed. There exists a feeling of slimy even after 10 cycles of rinsing, and therefore is not desired by the consumers, especially those with oily skin type.

Besides, the applicant found that, by simply reducing the hydrocarbon wax and oil emollients from the prior art, it is difficult to obtain a mild composition which has the cosmetic properties mentioned above, and is stable over time.

Thus there is a need for formulating a composition for treating keratin materials, in particular for cleansing keratin materials, with an improved rinsing speed, and stability.

Moreover, there is a need for formulating such a composition as mentioned above, with a good cleansing property, such as density of foam.

More particularly, there exists a need for formulating such a composition with an improved foaming volume, particularly in the existence of sebum, for example, on oily or greasy skin.

SUMMARY OF THE INVENTION

The applicant found such a need can be met by formulating a composition for treating keratin materials, comprising specific combination of surfactants, solid fatty acid(s), starch phosphates, and acrylic thickening polymer(s).

More specifically one aspect of the present invention is a composition comprising:
a) at least one amino acid surfactant;
b) at least one amphoteric or zwitterionic surfactant;
c) at least one solid fatty acid;
d) at least one starch phosphate; and
e) at least one acrylic thickening polymer.

The composition as described above is a composition for treating keratin materials, in particular, for caring for and/or making up keratin materials.

The composition as such is intended for cleansing of keratin materials, in particular the skin.

More particularly, one other aspect of the present invention is a process for treating keratin materials, in particular the skin and scalp, comprising the application to the keratin materials of the composition according to the invention.

Preferably, the process is intended for cleansing of keratin materials.

Particularly, the process comprises rinsing off the composition of the present invention after an optional period of time.

The invention also relates to the use of the composition according to the invention for cleansing keratin materials, in particular the skin.

By "keratin materials" we intend to mean human keratin materials and more specifically skin and scalp, and more particularly the skin of the face.

"Stable over time" is understood to mean compositions of the present invention which, after storage at all temperatures between 4° C. and 45° C. for 2 months, do not exhibit any macroscopic change in colour, smell or viscosity, any variation in pH or any variation in microscopic appearance.

Other subjects and characteristics, aspects and advantages of the invention will emerge even more clearly on reading the description and the examples that follows.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

DETAILED DESCRIPTION OF THE INVENTION

Amino Acid Surfactant(s)

The composition of the present invention comprises at least one amino acid surfactant.

In one embodiment, said amino acid surfactant is derived from a carboxylate salt of amino acid wherein the amine group situated on the α-carbon or β-carbon of an amino acid salt is acylated with a $C_8$ to $C_{22}$ fatty acid derivative.

The carboxylate salts of these amino acids can be formed by conventional means such as by neutralization of the respective amino acid with a base. The amine group situated on the α-carbon or β-carbon of the neutralized amino acid is acylated with a fatty acid halide (acyl halide) in the presence of a base via the well-known Schotten-Baumann reaction giving the amide, thus forming the desired surfactant reaction product, i.e. the amino acid surfactant. Suitable acyl halides for acylation of the amino acid carboxylate salt include acyl chlorides, bromides, fluorides, and iodides. The acyl halides can be prepared by reacting a saturated or unsaturated, linear or branched $C_8$ to $C_{22}$ fatty acid with a thionyl halide (bromide, chloride, fluoride, and iodide). Representative acyl halides include but are not limited to the acyl chlorides selected from decanoyl chloride, dodecanoyl chloride (lauroyl chloride), cocoyl chloride (coconut oil derived fatty acid chlorides) tetradecanoyl chloride (myristoyl chloride), hexadecanoyl chloride (palmitoyl chloride), octadecanoyl chloride (stearoyl chloride), 9-octadecenoyl chloride (oleoyl chloride), eicosanoyl chloride (arachidoyl chloride), docosanoyl chloride (behenoyl chloride), and any mixture thereof. Other acyl halides include the bromides, fluorides and iodides of the foregoing fatty acids. A method for preparing acyl halides as well as an alternative method for acylating amino acids is set forth in US Patent Application Publication No. 2008/0200704, published on Aug. 21, 2008, which application is incorporated herein by reference.

In one embodiment, said amino acid surfactant is represented by the formula (I):

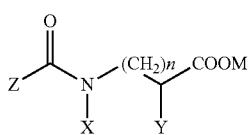

wherein:

Z represents a saturated or unsaturated, linear or branched hydrocarbon group having 8 to 22 carbon atoms, X is hydrogen or methyl group, n is 0 or 1, Y is selected from hydrogen, $-CH_3$, $-CH(CH_3)_2$, $-CH_2CH(CH_3)_2$, $-CH(CH_3)CH_2CH_3$, $-CH_2C_6H_5$, $-CH_2C_2H_4OH$, $-CH_2OH$, $-CH(OH)CH_3$, $-(CH_2)_4NH_2$, $-(CH_2)_3NHC(NH)NH_2$, $-CH_2C(O)O^-M^+$, $-(CH_2)_2C(O)OH$, $-(CH_2)_2C(O)O^-M^+$, and M is a salt-forming cation wherein COO is the counter-anion, such as for example sodium, potassium, ammonium, or triethanolamine.

Thus according to the present invention, the amino acid surfactant is represented by the formula (I),

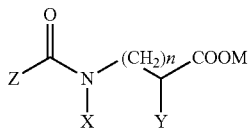

wherein:

Z represents a saturated or unsaturated, linear or branched hydrocarbon group having 8 to 22 carbon atoms, X is hydrogen or methyl group, n is 0 or 1, Y is selected from hydrogen, $-CH_3$, $-CH(CH_3)_2$, $-CH_2CH(CH_3)_2$, $-CH(CH_3)CH_2CH_3$, $-CH_2C_6H_5$, $-CH_2C_2H_4OH$, $-CH_2OH$, $-CH(OH)CH_3$, $-(CH_2)_4NH_2$, $-(CH_2)_3NHC(NH)NH_2$, $-CH_2C(O)O^-M^+$, $-(CH_2)_2C(O)OH$, $-(CH_2)_2C(O)O^-M^+$, and M is a salt-forming cation wherein COO is the counter-anion, such as for example sodium, potassium, ammonium, or triethanolamine.

In one embodiment, in formula (I):

Z represents a saturated or unsaturated, linear or branched $C_8$ to $C_{22}$ alkyl group, X is a hydrogen or methyl group, n is 0, Y is selected from hydrogen, $-(CH_2)_2C(O)OH$, $-(CH_2)_2C(O)O^-M^+$, and M is a salt-forming cation wherein COO is the counter-anion, such as for example sodium, potassium, ammonium, or triethanolamine.

According to a preferred embodiment of the invention, in the amino fatty acid of formula (I):

Z represents a saturated or unsaturated, linear or branched $C_8$ to $C_{22}$ alkyl group, X is a hydrogen or methyl group, n is 0, Y is selected from hydrogen, $-(CH_2)_2C(O)OH$, $-(CH_2)_2C(O)O^-M^+$, and M is a salt-forming cation wherein COO is the counter-anion, such as for example sodium, potassium, ammonium, or triethanolamine.

Examples of the amino acid surfactants are salt of alanine, arginine, aspartic acid, glutamic acid, glycine, isoleucine, leucine, lysine, phenylalanine, serine, tyrosine, valine, sarcosine, and any mixture thereof.

More specifically, mentions can be made of the amino acid surfactants such as dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alaninate, lauroyl β-alaninate, lauroyl methyl β-alaninate, myristoyl β-alaninate, potassium lauroyl methyl β-alaninate, sodium cocoyl alaninate, sodium cocoyl methyl β-alaninate and sodium myristoyl methyl β-alaninate palmitoyl glycinate, sodium lauroyl glycinate, sodium cocoyl glycinate, sodium myristoyl glycinate, potassium lauroyl glycinate, potassium cocoyl glycinate, potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate ammonium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof.

References can be made to the commercially available amino acid surfactant of, for example, acylsarcosinates, for instance the sodium lauroyl sarcosinate sold under the name Sarkosyl NL 97® by the company Ciba or sold under the name Oramix L 30® by the company SEPPIC, the sodium myristoyl sarcosinate sold under the name Nikkol Sarcosinate MN® by the company Nikkol or the sodium palmitoyl sarcosinate sold under the name Nikkol Sarcosinate PN® by the company Nikkol, or a mixture thereof.

Mentions of the preferred amino acid surfactant in the composition which is commercially available can be made to sodium lauroyl sarcosinate (ORAMIX L 30 sold by Seppic).

Preferably, the amino fatty acid surfactant is present in the composition in an amount ranging from 0.1% to 20% by weight, preferably from 0.5% to 15% by weight, more preferably from 1% to 10% by weight, relative to the total weight of the composition.

Amphoteric or Zwitterionic Surfactant(s)

The amphoteric or zwitterionic surfactant(s) that may be used in the present invention may be quaternized secondary or tertiary aliphatic amine derivatives containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of $(C_8-C_{20})$alkylbetaines, sulfobetaines, $(C_8-C_{20}$ alkyl)amido$(C_2-C_8$ alkyl) betaines and $(C_8-C_{20}$ alkyl)amido$(C_2-C_8$ alkyl)sulfobetaines.

Among the $(C_8-C_{20})$alkylbetaines, mentions may be made of behenylbetaine, cetyl betaine, cocoylbetaine, decylbetaine. From alkylbetaines, cocoylbetaine is preferred, for example the products sold by the company Rhodia under the tradename Mirataine® BB/FLA.

Among the optionally quaternized secondary or tertiary aliphatic amine derivatives that may be used, mention may also be made of the products of respective structures (A1) and (A2) below:

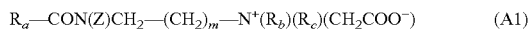

in which:

$R_a$ represents a $C_{10}-C_{30}$ alkyl or alkenyl group derived from an acid $R_a$—COOH preferably present in hydrolysed coconut oil, a heptyl group, a nonyl group or an undecyl group, $R_b$ represents a β-hydroxyethyl group, $R_c$ represents a carboxymethyl group;

m is equal to 0, 1 or 2,

Z represents a hydrogen atom or a hydroxyethyl or carboxymethyl group;

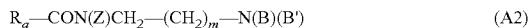

in which:

B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom, B' represents —(CH$_2$)$_z$—Y', with z=1 or 2, and Y' representing —COOH, —COOZ', —CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, $R_{a'}$ represents a $C_{10}-C_{30}$ alkyl or alkenyl group of an acid $R_a$COOH preferably present in hydrolysed linseed oil or coconut oil, an alkyl group, in particular a $C_{17}$ alkyl group, and its iso form, or an unsaturated $C_{17}$ group.

The compounds corresponding to formula (A1) are preferred.

Among the compounds corresponding to formula (A1), mentions may be made of cocamidopropyl betaine, for example the product sold under the tradename Dehyton PK 45 by Cognis (BASF).

Use may also be made of the compounds of formula (A3):

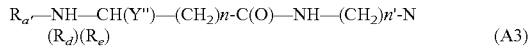

in which:

$R_{a''}$ represents a $C_{10}-C_{30}$ alkyl or alkenyl group of an acid $R_{a''}$—C(O)OH preferably present in hydrolysed linseed oil or coconut oil;

Y" represents the group C(O)OH, —C(O)OZ", —CH$_2$—CH(OH)—SO$_3$H or the group —CH$_2$—CH(OH)—SO$_3$—Z", with Z" representing a cationic counterion resulting from an alkali metal or alkaline-earth metal, such as sodium, an ammonium ion or an ion resulting from an organic amine;

$R_d$ and $R_e$ represent, independently of each other, a $C_1-C_4$ alkyl or hydroxyalkyl radical; and n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name Chimexane HB.

Preferably, the amphoteric surfactants are chosen from $(C_8-C_{20})$alkylbetaines, $(C_8-C_{20})$alkylamido$(C_1-C_6)$alkylbetaines, and mixtures thereof.

More preferably, the amphoteric or zwitterionic surfactant is chosen from cocamidopropyl betaine, cocoylbetaine, or a mixture thereof.

Advantageously, the amphoteric or zwitterionic surfactant is present in the composition in an amount ranging from 0.5% to 20% by weight, preferably from 1% to 15% by weight, relative to the total weight of the composition.

Solid Fatty Acid

The composition of the present invention comprises at least one solid fatty acid.

The term "fatty alcohol" means a long-chain aliphatic alcohol comprising from 10 to 40 carbon atoms, preferably from 12 to 30 carbon atoms, and comprising at least one group COOH. These fatty acids are neither oxyalkylenated nor glycerolated.

The "solid fatty acids" are solid at room temperature (25° C.) and at atmospheric pressure (760 mmHg or 1 atm.); they are water-insoluble, i.e. they have a solubility in water of less than 1% by mass and preferably less than 0.5% by weight.

Preferably, the solid fatty acids are of structure R—COOH with R denoting a saturated or unsaturated, linear alkyl group, optionally substituted with one or more hydroxyl groups, comprising from 12 to 30 carbon atoms.

Preferably, the solid fatty acids used in the present invention are selected from fatty acids having from 12 to 20 carbon atoms.

Mentions may be made of, as solid fatty acids, are capric acid, lauric acid, myristic acid, myristoleic acid, palmitic acid, palmitoleic acid, sapienic acid, stearic acid, oleic acid, elaidic acid, vaccenic acid, linoleic acid, α-linolenic acid, arachidic acid, arachidonic acid, eicosapentaenoic acid, behenic acid, erucic acid, docosahexaenoic acid, lignoceric acid, cerotic acid, or a mixture thereof.

More preferably, according to the present invention, the solid fatty acid is selected from linear saturated fatty acids having from 12 to 20 carbon atoms, such as lauric acid, myristic acid, palmitic acid, stearic acid, arachidic acid, or a mixture thereof.

More particularly, the solid fatty acids are selected from lauric acid, myristic acid, palmitic acid, stearic acid, or a mixture thereof.

The fatty acids may be a mixture, which means, for example, that several species may coexist in a commercial product, especially of different chain lengths, in the form of a mixture.

Mentions of such mixture of fatty alcohols may be made of lauric acid, which is commercially available under the tradename Kortacid 1299 from the company Pacific Oleochemicals.

According to one embodiment, the solid fatty acid is present in the composition in an amount ranging from 0.1% to 10%, preferably from 0.5 to 5% by weight, relative to the total weight of the composition.

Starch Phosphates

The composition of the present invention comprises at least one starch phosphate, or a mixture thereof.

The starch phosphates that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the plant origin of the starches.

The starch molecules used in the present invention may originate from a plant source such as cereals, tubers, roots, legumes and fruit. Thus, the starch(es) may originate from a plant source chosen from corn, pea, potato, sweet potato, banana, barley, wheat, rice, oat, sago, tapioca and sorghum. The starch is preferably derived from corn.

It is also possible to use the starch hydrolysates mentioned above.

Starch phosphates are generally in the form of a white powder, whose elemental particle size ranges from 3 to 100 microns.

The starches used in the composition of the invention may be chemically modified via one or more of the following reactions: pregelatinization, oxidation, crosslinking, esterification, heat treatments.

In particular, the crosslinking reaction is preferred. This reaction is performed by crosslinking with functional agents capable of reacting with the hydroxyl groups of the starch molecules, which will thus bond together (for example with glyceryl and/or phosphate groups).

More particularly, the starch phosphate is chosen from: monostarch phosphates of formula (II),

distarch phosphates of formula (III),

tristarch phosphates of the formula (IV),

or a mixture thereof,
wherein:
Am means starch;
X represents alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

Preferably, the starch phosphate of the present invention is chosen from distarch phosphates of formula (III) described above.

Mentions may be made of the distarch phosphates, for example, the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea (gelatinized hydroxypropyl corn distarch phosphate) by the company Akzo Nobel.

Preferably, the starch phosphate is present in the composition of the present invention in an amount ranging from 0.05% to 10% by weight, preferably from 0.1% to 7% by weight, and better still from 0.5% to 5% by weight, relative to the total weight of the composition.

Acrylic Thickening Polymer

The compositions of the invention comprise at least one acrylic thickening polymer.

For the purposes of the present invention, the term "acrylic polymer" means a polymer resulting from the polymerization of at least one or more monomers having the structure:

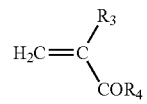

$R_3$ denoting a hydrogen atom or a linear or branched $C_1$-$C_4$ alkyl radical, $R_4$ denoting a hydrogen atom, a linear or branched $C_1$-$C_4$ alkyl radical, a radical $NR_5R_6$, or a linear or branched $C_1$-$C_{30}$ alkoxy radical, optionally substituted with one or more hydroxyl radicals or with a quaternary ammonium radical, $R_5$ and $R_6$ denote a hydrogen atom or an optionally oxyalkylenated $C_1$-$C_{30}$ alkyl radical, the alkyl radical possibly comprising a sulfonic group.

Preferably, $R_3$ denotes a hydrogen atom or a methyl radical.

For the purposes of the present invention, the term "thickening polymer" means a polymer having, as a 1% by weight solution or dispersion of active material in water or in ethanol at 25° C., a viscosity of greater than 0.2 poise at a shear rate of 1 s$^{-1}$. The viscosity is measured with a Haake RS600 viscometer from Thermo Electron. This viscometer is a controlled-stress viscometer with cone-plate geometry (for example of diameter 60 mm).

The thickening polymers are especially chosen from:
(a) acrylic associative polymers;
(b) crosslinked acrylic acid homopolymers;
(c) crosslinked copolymers of (meth)acrylic acid and of a ($C_1$-$C_6$)alkyl acrylate;
(d) nonionic homopolymers and copolymers containing ethylenically unsaturated monomers of ester and/or amide type;
(e) ammonium acrylate homopolymers or copolymers of ammonium acrylate and of acrylamide;
(f) (meth)acrylamido($C_1$-$C_4$)alkylsulfonic acid homopolymers and copolymers;
(g) crosslinked methacryloyl($C_1$-$C_4$)alkyltri($C_1$-$C_4$)alkylammonium homopolymers and copolymers.

According to the invention, the expression "associative polymers" means amphiphilic polymers comprising at least one fatty chain, i.e., a hydrophobic portion and at least one hydrophilic portion.

The number of hydrophobic portions may be smaller compared with the remainder of the polymeric chain, and may be located laterally of the chain and be distributed in a random manner (random copolymers) or be distributed in the form of blocks or grafts (block copolymers or sequence copolymers).

Water-soluble polymers or hydrodispersible polymers may be used. Preferably, the amphiphilic polymers used in the present invention are not cross-linked.

The associative polymers of the invention are anionic and comprise, as monomers, at least one unsaturated carboxylic acid. Unsaturated carboxylic acids which may be used in the polymers of the invention are preferably selected from the group formed by acrylic, methacrylic, crotonic, itaconic and maleic acids.

The expression "fatty chain" as used in the present invention means a linear or branched hydrocarbon group containing 8 to 30 carbon atoms.

Preferably, according to an embodiment, the acrylic thickening polymer of the present invention is selected from the group consisting of acrylic associative polymers, crosslinked copolymers of (meth)acrylic acid and of a ($C_1$-$C_6$) alkyl acrylate, or a mixture thereof.

Acrylic associative polymers (a) that may be used according to the invention are acrylic associative polymers chosen from nonionic amphiphilic polymers comprising at least one fatty chain and at least one hydrophilic unit; anionic amphiphilic polymers comprising at least one hydrophilic unit and at least one fatty-chain unit; cationic amphiphilic polymers comprising at least one hydrophilic unit and/or at least one fatty-chain unit; amphoteric amphiphilic polymers comprising at least one hydrophilic unit and at least one fatty-chain unit; the fatty chains containing from 10 to 30 carbon atoms; or a mixture thereof.

Preferably, the acrylic associative polymer is chosen from anionic amphiphilic polymers comprising at least one hydrophilic unit and at least one fatty-chain unit.

The following anionic acrylic associative polymers of the invention may be cited:

copolymers comprising at least one hydrophilic motif and at least one fatty chain allyl ether motif, the hydrophilic motif of which is constituted by a vinyl carboxylic acid and more particularly by an acrylic acid or a methacrylic acid or mixtures thereof, and the fatty chain allyl ether motif of which corresponds to the monomer with the following formula (V):

$$CH_2=CR'CH_2OB_nR \quad (V)$$

in which:

R' designates H or $CH_3$;

B designates the ethyleneoxy radical;

n is zero or designates a whole number from 1 to 100;

R designates a hydrocarbon radical selected from alkyl, arylalkyl, aryl, alkylaryl and cycloalkyl radicals containing 8 to 30 carbon atoms, preferably 10 to 24, and more particularly 12 to 18 carbon atoms.

A more particularly preferred motif with formula (V) is a motif in which R' designates H, n equals 10 and R designates a stearyl radical ($C_{18}$).

Anionic associative polymers of this type have been described and prepared by an emulsion polymerization method in the patent EP-A-0 216 479.

Particularly preferred polymers of the present invention include polymers formed by 20% to 60% by weight of acrylic acid and/or methacrylic acid, 5% to 60% by weight of lower alkyl (meth)acrylates, 2% to 50% by weight of fatty chain allyl ether with formula (V) and 0 to 1% by weight of a cross-linking agent which is a well-known copolymerizable unsaturated polyethylenic monomer such as diallyl phthalate, allyl (meth)acrylate, divinylbenzene, (poly)ethyleneglycol dimethacrylate or methylene-bis-acrylamide.

Of these latter, the following are particularly preferred: cross-linked terpolymers sold by ALLIED COLLOIDS under trade names SALCARE SC 80® and SALCARE SC90® which are 30% aqueous emulsions of a cross-linked terpolymer of methacrylic acid, ethyl acrylate and steareth-10-allyl ether (40/50/10).

It is also possible to cite the products RHOEVIS CR, —CR3 and —CRX proposed by ALLIED COLLOIDS as polymers in this product category;

methacrylic acid/alkyl acrylate/polyoxyethylenated lauryl acrylate terpolymers, such as RHEO 2000 sold by COATEX;

methacrylic acid/alkyl acrylate/polyoxyethylenated stearyl methacrylate copolymers, such as ACRYSOL 22 (or ACULYN 22 or ACRYSOL ICS), ACRYSOL 25 and DW-1206A sold by ROHM & HAAS;

methacrylic acid/alkyl acrylate/polyoxyethylenated nonylphenol acrylate copolymers such as RHEO 3000 sold by COATEX;

methacrylic acid/butyl acrylate/hydrophobic monomer copolymers comprising a fatty chain such as the 8069-146A product sold by NATIONAL STARCH;

copolymers comprising at least one hydrophilic motif of the unsaturated olefinic carboxylic acid type and at least one hydrophobic motif of the $C_{10}$-$C_{30}$ alkyl ester of an unsaturated carboxylic acid type.

Preferred associative polymers are as follows:

acrylic acid/ethyl $C_1$-$C_8$ acrylate/stearyl methacrylate polyoxyethylenated, for example, using 20 moles of ethylene oxide such as the product sold under the trade name "ACRYSOL ICS or ACRYSOL ZZ or ACULYN 22" by ROHM & HAAS.

Depending on their nature, the associative polymers of the invention may be used in the form of aqueous solutions or in the form of aqueous dispersions.

Among the crosslinked copolymers of (meth)acrylic acid and of $C_1$-$C_6$ alkyl acrylate (c) that may be mentioned is the product sold under the name Viscoatex 538C by the company Coatex, which is a crosslinked copolymer of methacrylic acid and of ethyl acrylate as an aqueous dispersion containing 38% active material, or the product sold under the name Aculyn 33 by the company Rohm & Haas, which is a crosslinked copolymer of acrylic acid and of ethyl acrylate as an aqueous dispersion containing 28% active material. Mention will be made more particularly of the crosslinked methacrylic acid/ethyl acrylate copolymer in the form of an aqueous 30% dispersion manufactured and sold under the name Carbopol Aqua SF-1 by the company Noveon.

Preferably, mentions may be made, among the crosslinked copolymers of (meth)acrylic acid and of $C_1$-$C_6$ alkyl acrylate (c), a crosslinked copolymer of acrylic acid and of ethyl acrylate is used.

According to a preferred embodiment, the acrylic thickening polymer is present in the composition in an amount ranging from 0.1% to 10% by weight, preferably from 0.5% to 5% by weight, relative to the total weight of the composition.

Advantageously, the present invention relates to a composition for cleansing a keratin material, comprising, relative to the total weight of the composition:

A) from 0.5% to 15% by weight of at least one amino acid surfactant of formula (I),

(I)

wherein:

Z represents a saturated or unsaturated, linear or branched $C_8$ to $C_{22}$ alkyl group, X is a hydrogen or methyl group, n is 0, Y is selected from hydrogen, —$(CH_2)_2C(O)OH$, —$(CH_2)_2C(O)O^-M^+$, and M is a salt-forming cation wherein COO is the counteranion, such as for example sodium, potassium, ammonium, or triethanolamine, B) from 1% to 15% by weight of at least one amphoteric or zwitterionic surfactant selected from the group consisting of $(C_8$-$C_{20})$alkylbetaines, $(C_8$-$C_{20})$alkylamido $(C_1$-$C_6)$alkylbetaines, and mixtures thereof;

C) from 0.5% to 5% by weight of at least one solid fatty acid having from 12 to 20 carbon atoms;

D) from 0.1% to 7% by weight of at least one distarch phosphate of formula (III), $$Am—O—PO—(OX)—O—Am \quad (III),$$

wherein:

Am means starch;

X represents alkali metals, ammonium salts, amine salts, or ammonium salts derived from basic amino acids; and E) 0.5% to 5% by weight of at least one acrylic thickening polymer selected from the group consisting of acrylic associative polymers, crosslinked copolymers of (meth)acrylic acid and of a $(C_1$-$C_6)$alkyl acrylate, or a mixture thereof.

Method and Use

The composition of the present invention can be used for a process for cleansing keratin materials, such as the skin and scalp, in particular the face, by being applied to the keratin materials.

Particularly, the process comprises rinsing off of the composition of the present invention by water after an optional period of time.

The present invention also relates to a use of the composition according to the present invention, for cleansing keratin materials, especially for the skin and scalp, and more particularly for the face.

The present invention relates to a process for cleansing a keratin material, comprising the application, to the surface of the said keratin material, of at least one composition of the invention, wherein the keratin material is preferably skin and scalp, in particular face.

The examples that follow are aimed at illustrating the compositions and processes according to this invention, but are not in any way a limitation of the scope of the invention.

EXAMPLES

Example 1

Formulation Example

The following formulas were prepared:

|  |  | % by weight by active | |
|---|---|---|---|
| Phase | INCI name (tradename and supplier) | Invention formula A | Comparative formula B |
| A | SODIUM LAUROYL SARCOSINATE (Oramix ™ L 30 from Seppic) | 2.2 | 2.2 |
| E | COCO-BETAINE (Dehyton AB 30 from BASF) | 4.0 | 4.0 |
| C | LAURIC ACID (Lauric acid POFAC 1299 from Southern Acids) | 1.7 | 1.7 |
| D | HYDROXYPROPYL STARCH PHOSPHATE (Structure ZEA from Akzo Nobel) | 1 | 1 |
| B | ACRYLATES COPOLYMER (crosslinked copolymer of acrylic acid and of ethyl acrylate as an aqueous dispersion containing 28% active material, Aculyn 33 from Rohm and Haas (Dow Chemical)) | 1.5 | 0 |
| B | POLYQUATERNIUM-55 (polymeric quaternary ammonium chloride formed by the reaction of vinylpyrrolidone, dimethylaminopropyl methacrylamide and methacryloylaminopropyl lauryldimonium chloride, Styleze W-17L from ISP) | 0 | 1.5 |
| C | POTASSIUM HYDROXIDE | 1.0 | 1.0 |
| A | WATER | QS to 100 | QS to 100 |

Comparative formula B contains a polymer other than the one claimed in the invention.

The formulas were prepared by mixing phase A and heating to 75° C., adding phase B to phase A at 70° C. and mixing for 5 min, adding phase C to the mixture of phase A and B at 65° C. and mixing for 5 min, then adding phase D and E, respectively, to the mixture obtained above, at 65° C., and mixing for 10 minutes.

The machine used for mixing is homogenizer VMI sold by the company i-Tech.

The facial cleanser C according to the invention and comparative cleanser D were prepared:

|  |  | % by weight by active | |
|---|---|---|---|
| Phase | INCI name (tradename and supplier) | Facial cleanser C | Comparative cleanser D |
| A | WATER | QS to 100 | QS to 100 |
| A | SODIUM LAUROYL SARCOSINATE (Oramix ™ L 30 from Seppic) | 2.2 | 0 |
| A | SODIUM LAURYL SULFATE | 0 | 2.8 |
| A | DISODIUM LAURETH SULFOSUCCINATE | 0 | 2.6 |
| A | TETRASODIUM EDTA | 0.3 | 0.3 |
| A | PHENOXYETHANOL | 0.3 | 0.3 |
| A | ETHYLHEXYLGLYCERIN | 0.1 | 0.1 |

-continued

| Phase | INCI name (tradename and supplier) | % by weight by active | |
|---|---|---|---|
| | | Facial cleanser C | Comparative cleanser D |
| A | COCAMIDE MEA | 1.0 | 1.0 |
| B | GLYCOL DISTEARATE | 1.0 | 1.0 |
| C | ACRYLATES COPOLYMER (crosslinked copolymer of acrylic acid and of ethyl acrylate as an aqueous dispersion containing 28% active material, Aculyn 33 from Rohm and Haas (Dow Chemical)) | 1.5 | 1.5 |
| C | ACRYLATES/STEARETH-20 METHACRYLATE COPOLYMER (crosslinked copolymers of (meth)acrylic acid and of $C_1$-$C_6$ alkyl acrylate, Aculyn 22 from Rohm and Haas Chemical) | 0.5 | 0.5 |
| C | WATER | 6.0 | 6.0 |
| D | LAURIC ACID (Lauric acid POFAC 1299 from Southern Acids) | 1.7 | 2.0 |
| D | POTASSIUM HYDROXIDE | 1.0 | 1.0 |
| D | WATER | 15 | 15 |
| E | HYDROXYPROPYL STARCH PHOSPHATE (Structure ZEA from Akzo Nobel) | 1.0 | 1.0 |
| F | COCO-BETAINE (Dehyton AB 30 from BASF) | 4.0 | 4.0 |
| G | RED 4 | 0.0004 | 0.0004 |
| G | WATER | 1.0 | 1.0 |
| H | PEG-90M (Polyox WSR 301 Amerchol from Amerchol (Dow Chemical)) | 0.2 | 0.2 |
| H | WATER | 10.0 | 10.0 |
| I | FRAGRANCE | 0.3 | 0.3 |

The comparative cleanser D contains anionic surfactants instead of the amino acid surfactant as claimed in the present invention.

The above face cleansers were prepared following the steps of:
mixing phase A, heat it to 75° C.,
adding phase B at 75° C. in phase A and mixing for 5 min,
adding phase C at 70° C. and mixing for 5 min;
adding pre-phase D at 65° C. and mixing for 5 min;
adding phase E at 65° C. and mixing for 10 min;
adding phase F at 65° C. and mixing for 10 min;
adding phase G at 50° C.;
adding pre-phase H and I below 40° C.

The machine used for mixing is homogenizer VMI sold by the company i-Tech.

Example 2

Evaluation Example

The rinsing-speed as well as density of foam of the invention and comparative formulas were evaluated by 5 consumers, by using the invention and comparative formulas as a face cleanser.

0.5 g of the invention and comparative formulas were applied on the face of 5 women consumers, respectively, and the face with the formulas were massaged for X minutes by the consumers. Then the faces were rinsed by warm water. After 10 minutes, the scores were given to the following effects:

Rinsing speed: the period of time when there is no feeling of slim on the skin, which represents that the face were rinsed and clean; it is represented by number of cycles. The less the number of cycles, the faster the rinsing speed is.

By "cycle" we intend to mean an action of rinsing the facial skin using hands, in particular using fingers to wash the facial skin by turning around on the cheeks or from forehead to the bottom of cheeks.

Density of foam: the density of foam was evaluated by the consumers when massaging the faces wherein the invention and comparative formulas were applied, respectively. More particularly, the density of the foam were evaluated by the consumers, during the application of the formulas, by pressing the foam between hands and facial skin, after 40 rounds of rubbing the facial skin where the invention and comparative formulas were applied, respectively.

Scores 1 to 15 were given by the consumers to the density of foam. The higher the score is given, the better density of foam of the formula is. Stability of the invention and comparative formulas were evaluated by storing the formulas at 4° C., 20° C., 40° C., and 45° C. for 2 months.

The results were as follow:

| Items | Invention formula A | Invention formula C | Comparative formula B |
|---|---|---|---|
| Rinsing-speed stability | 5 cycles stable | 5 cycles stable | 10 cycles Unstable at 25° C. in 2 month |
| Density of foam | 10 | 10 | 5 |

It is observed from the results listed above, that the invention formula A and C show much better rinsing-speed, good stability, as well as improved density of foam, comparing to the comparative formula B.

Besides, the evaluation of foaming volume of the cleanser C and D in the existence of sebum was performed.

14.2 g of cleansers C and D were added respectively to 85.3 g of water, and 0.5 g of simulated sebum were added in both mixtures, respectively.

Then the mixtures were blended using Philips Blender (HR2024, 220V, 50 Hz, 400 W), using Gear 1 for 20 seconds.

The foam generated during the blending steps was measured in a 1000 ml measuring cylinder.

Finally, the volume of foam was recorded.

The simulated sebum is composed of 0.14 g of myristic acid, 0.25 g of triglyceride, and 0.11 g of squalene. The simulated sebum was a simulation of sebum generated on facial skin.

The results are as follow:

| Cleanser | Foaming volume (ml) |
|---|---|
| C | 370 |
| D | 225 |

It is observed that, with less amount of surfactant, the invention facial cleanser C presents a much better foaming volume, comparing to the comparative cleanser D, which contains higher amount of anionic surfactants, which are known for their foaming properties.

The invention claimed is:
1. A composition comprising:
a) at least one amino acid surfactant;
b) at least one amphoteric or zwitterionic surfactant;
at least one solid fatty acid;
d) at least one starch phosphate; and e) at least one acrylic thickening polymer selected from crosslinked copolymers of (meth)acrylic acid and of a ($C_1$-$C_6$)alkyl acrylate.

2. The composition of claim 1, wherein the amino acid surfactant is selected from a compound of formula (I),

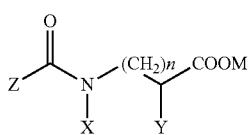

wherein in formula (I):
- Z represents a saturated or unsaturated, linear or branched hydrocarbon group having 8 to 22 carbon atoms,
- X is hydrogen or methyl group,
- n is 0 or 1,
- Y is selected from the group consisting of hydrogen, —$CH_3$, —$CH(CH_3)_2$, —$CH_2CH(CH_3)_2$, —$CH(CH_3)CH_2CH_3$, —$CH_2C_6H_5$, —$CH_2C_2H_4OH$, —$CH_2OH$, —$CH(OH)CH_3$, —$(CH_2)_4NH_2$, —$(CH_2)_3NHC(NH)NH_2$, —$CH_2C(O)O^-M^+$, —$(CH_2)_2C(O)OH$, and —$(CH_2)_2C(O)O^-M+$, and
- M is a salt-forming cation wherein COO is the counteranion.

3. The composition of claim 1, wherein the amino acid surfactant is selected from acylsarcosinates.

4. The composition of claim 1, wherein the amino acid surfactant is present in the composition in an amount ranging from 0.1% to 20% by weight, relative to a total weight of the composition.

5. The composition of claim 1, wherein the amphoteric or zwitterionic surfactant is selected from the group consisting of ($C_8$-$C_{20}$)alkylbetaines, ($C_8$-$C_{20}$)alkylamido($C_1$-$C_6$)alkylbetaines, and mixtures thereof.

6. The composition of claim 1, wherein the amphoteric or zwitterionic surfactant is present in the composition in an amount ranging from 0.5% to 20% by weight, relative to a total weight of the composition.

7. The composition of claim 1, wherein the solid fatty acid is selected from fatty acids having from 12 to 20 carbon atoms.

8. The composition of claim 1, wherein the solid fatty acid is present in the composition in an amount ranging from 0.1% to 10%, relative to a total weight of the composition.

9. The composition of claim 1, wherein the starch phosphate is selected from the group consisting of:
monostarch phosphates of formula (II),

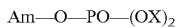  (II), distarch phosphates of formula (III),

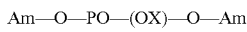  (III), tristarch phosphates of the formula (IV),

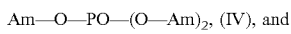 (IV), and mixtures thereof, wherein:
- Am means starch; and
- X represents alkali metals, ammonium salts, amine salts, or ammonium salts derived from basic amino acids.

10. The composition of claim 9, wherein the starch phosphate is selected from distarch phosphates of formula (III).

11. The composition of claim 10, wherein the starch phosphate is gelatinized hydroxypropyl corn distarch phosphate.

12. The composition of claim 1, wherein the starch phosphate is present in the composition in an amount ranging from 0.05% to 10% by weight, relative to a total weight of the composition.

13. The composition of claim 1, wherein the acrylic thickening polymer is present in the composition in an amount ranging from 0.1% to 10% by weight, relative to a total weight of the composition.

14. A composition for cleansing a keratin material, comprising, relative to a total weight of the composition:

A) from 0.5% to 15% by weight of at least one amino acid surfactant of formula (I),

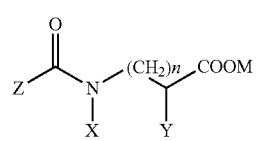

wherein:
- Z represents a saturated or unsaturated, linear or branched $C_8$ to $C_{22}$ alkyl group,
- X is a methyl group,
- n is 0,
- Y is selected from the group consisting of hydrogen, —$(CH_2)_2C(O)OH$, and —$(CH_2)_2C(O)O^-M^+$, and
- M is a salt-forming cation wherein COO is the counteranion, B) from 1% to 15% by weight of at least one amphoteric or zwitterionic surfactant selected from the group consisting of ($C_8$-$C_{20}$)alkylbetaines, ($C_8$-$C_{20}$)alkylamido ($C_1$-$C_6$)alkylbetaines, and mixtures thereof;

C) from 0.5% to 5% by weight of at least one solid fatty acid having from 12 to 20 carbon atoms;

D) from 0.1% to 7% by weight of at least one distarch phosphate of formula (III),

wherein:
- Am means starch; and
- X represents alkali metals, ammonium salts, amine salts, or ammonium salts derived from basic amino acids; and E) from 0.5% to 5% by weight of at least one acrylic thickening polymer selected from crosslinked copolymers of (meth)acrylic acid and of a ($C_1$-$C_6$)alkyl acrylate.

15. A process for cleansing keratin materials, comprising applying to the keratin material the composition of claim 1.

16. The process for cleansing keratin materials of claim 15, comprising applying the composition to keratin material of a face.

* * * * *